US010737998B2

(12) United States Patent
Hirschberg et al.

(10) Patent No.: US 10,737,998 B2
(45) Date of Patent: Aug. 11, 2020

(54) METHODS FOR CONVERTING FLUORINATED COMPOUNDS

(71) Applicant: 3M INNOVATIVE PROPERTIES COMPANY, St. Paul, MN (US)

(72) Inventors: Markus E. Hirschberg, Burgkirchen (DE); Klaus Hintzer, Kastl (DE); Zai-Ming Qiu, Woodbury, MN (US); Gerd-Volker Röschenthaler, Bremen (DE); Romana Pajkert, Breman (DE); Sergey Tverdomed, Breman (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 16/065,454

(22) PCT Filed: Dec. 12, 2016

(86) PCT No.: PCT/US2016/066196
§ 371 (c)(1),
(2) Date: Jun. 22, 2018

(87) PCT Pub. No.: WO2017/112445
PCT Pub. Date: Jun. 29, 2017

(65) Prior Publication Data
US 2019/0144370 A1 May 16, 2019

Related U.S. Application Data

(60) Provisional application No. 62/387,481, filed on Dec. 24, 2015.

(51) Int. Cl.
| C07C 51/58 | (2006.01) |
| C07C 69/96 | (2006.01) |
| C07C 59/135 | (2006.01) |
| C07C 68/00 | (2020.01) |
| C07C 45/42 | (2006.01) |
| C07C 67/14 | (2006.01) |
| C07C 51/04 | (2006.01) |
| C07C 51/00 | (2006.01) |
| C07C 67/00 | (2006.01) |
| B01J 23/28 | (2006.01) |

(52) U.S. Cl.
CPC .............. *C07C 51/58* (2013.01); *B01J 23/28* (2013.01); *C07C 45/42* (2013.01); *C07C 51/00* (2013.01); *C07C 51/04* (2013.01); *C07C 59/135* (2013.01); *C07C 67/00* (2013.01); *C07C 67/14* (2013.01); *C07C 68/00* (2013.01); *C07C 69/96* (2013.01); *B01J 2523/55* (2013.01); *B01J 2523/68* (2013.01)

(58) Field of Classification Search
None
See application file for complete search history.

(56) References Cited

U.S. PATENT DOCUMENTS

| 3,250,808 | A | 5/1966 | Moore, Jr. |
| 4,987,254 | A | 1/1991 | Schwertfeger et al. |
| 5,260,492 | A | 11/1993 | Feiring |
| 8,440,858 | B2 | 5/2013 | Zipplies |
| 8,633,328 | B2 | 1/2014 | Zipplies |
| 2007/0267464 | A1* | 11/2007 | Vitcak .................. C07D 307/20 228/203 |
| 2011/0245520 | A1 | 10/2011 | Zipplies |

FOREIGN PATENT DOCUMENTS

| WO | WO 1995-32174 | 11/1995 |
| WO | WO 2007-136948 | 11/2007 |
| WO | WO 2009-042853 | 4/2009 |
| WO | WO 2010-071730 | 6/2010 |
| WO | WO 2011-050131 | 4/2011 |
| WO | WO 2011-066156 | 6/2011 |
| WO | WO 2017-112629 | 6/2017 |

OTHER PUBLICATIONS

Shipilov et al., Russian J. of Organic Chem, 2002, 39:7, 975-978 (Year: 2002).*
Stockburger et al., J. Am. Chem. Soc., 1971, 93:14, 3332-3336 (Year: 1971).*
Afsharpour, "Synthesis, characterization and catalytic activity of a new peroxomolybdenum(VI) complex-based coordination polymer", Applied Catalysis A: General, Aug. 2007, vol. 327, No. 2, pp. 205-210.

(Continued)

*Primary Examiner* — Clinton A Brooks
*Assistant Examiner* — Kofi Adzamli
(74) *Attorney, Agent, or Firm* — Thomas M. Spielbauer

(57) ABSTRACT

Methods of converting a fluorinated compound into a fluorinated acyl fluoride or derivative thereof, the method including reacting the fluorinated compound with a catalytic amount of at least one transition metal compound and an oxygen-containing compound to form the fluorinated acyl fluoride or derivative thereof. Compounds formed using such methods are also included, including for example <Insert chemical formulas here as they appear in the electronic copy.> and derivatives thereof, or combinations thereof.

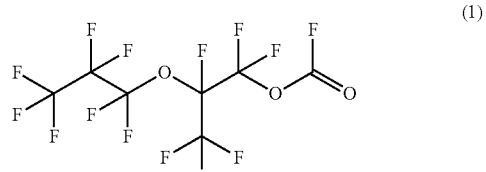

(1)

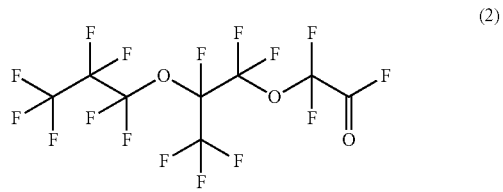

(2)

25 Claims, No Drawings

(56) References Cited

OTHER PUBLICATIONS

Czarnowski, "The 1,2-Fluorine Atom Migration in The Epoxide Of 1,1 Dichlorodifluoroethene. The Infrared Spectrum of Dichlorofluoroacetyl Fluoride", Journal of Fluorine Chemistry, 1990, vol. 47, pp. 193-198.

Dlouha, "Reactivity study of 1,1,2,4,4,5,7,7,8,8,9,9,9-tridecafluoro-5-trifluoromethy1-3, 6-dioxanon-1-ene in nucleophilic reactions: fluorination properties of secondary amine adducts", Journal of Fluorine Chemistry, 2002, vol. 117, pp. 149-159, XP4389690A.

England, "Reactions of Amines with a Dimer of Hexafluoropropene and Perfluorovinyl Sulfide prepared with Hexafluoropropene", Journal of Fluorine Chemistry, Jun. 1981, vol. 17, pp. 265-288.

Feiring, "Fluorinated Vinyl Monomers", Organofluorine Chemistry: Principles and Commercial Application, (Edited by Bank et al.), 1994, pp. 341-342.

Furin, "Reaction of 1,1,2-trifluoro-2-hexafluoro-2'-(heptafluoropropoxy)-propoxyethylene with amines or alcohols", Journal of Fluorine Chemistry, 2000, vol. 106, pp. 13-24, XP55360491A.

Herbert, "Olefin epoxidations in the ionic liquid [$C_4$mim][$PF_6$] catalysed by oxodiperoxomolybdenum species in situ generated from molybdenum trioxide and urea—hydrogen peroxide: The synthesis and molecular structure of [Mo(O)($O_2$)$_2$(4-MepyO)$_2$]•$H_2O$", Polyhedron, Dec. 2009, vol. 28, No. 18, pp. 3929-3934.

Methods for Converting Fluorinated Compounds, An IP.com Prior Art Database Technical Disclosure, IP.com No. 000244826, 7 pages.

Mimoun, "Vanadium(V) Peroxo Complexes. New Versatile Biomimetic Reagents for Epoxidation of Olefins and Hydroxylation of Alkanes amd Aromatic Hydrocarbons", Journal of the American Chemical Society, 1983, vol. 105, No. 10, pp. 3101-3110.

Park, "Fluorinated C-Nitroso Compounds. II The Reaction of Nitric Oxide with Some Fluoroolefins in the Presence of Ferric Chloride", The Journal of Organic Chemistry, Sep. 1961, vol. 26, No. 9, pp. 3319-3323, XP55384824A.

Pola, "CW $CO_2$ Laser Driven Oxidation of Some Perhalogeno-Cycloalkenes", Collection of Czechoslovak Chemical Communications, 1991, vol. 56, pp. 398-405, XP55386729A.

Shipilov, "Selective Hydrolysis of Pentafluorobenzotrichloride", Russian Journal of Organic Chemistry, 2003, vol. 39, No. 7, pp. 975-978, XP2422334A.

Stockburger, "Reaction of Oxygen Atoms with 1,3-Perfluorobutadiene", Journal of the American Society, Jul. 1971, vol. 93, No. 14, pp. 3331-3336.

Toneli, "Photolysis of perfluoroacyl fluorides", Journal of Fluorine Chemistry, 2000, vol. 101, pp. 117-123, XP4244505A.

International Search Report for PCT International Application No. PCT/US2016/066196, dated Jul. 26, 2017, 6 pages.

\* cited by examiner

METHODS FOR CONVERTING FLUORINATED COMPOUNDS

CROSS REFERENCE TO RELATED APPLICATIONS

This application is a national stage filing under 35 U.S.C. 371 of PCT/US2016/066196, filed Dec. 12, 2016, which claims the benefit of Provisional Application No. 62/387,481, filed Dec. 24, 2015, the disclosure of which is incorporated by reference in their entirety herein.

FIELD

The present disclosure relates to synthetic methods and compounds formed using such disclosed synthetic methods.

SUMMARY

Disclosed herein are methods of converting a fluorinated compound into a fluorinated acyl fluoride or derivative thereof, the method comprising: reacting the fluorinated compound with a catalytic amount of at least one transition metal compound and an oxygen-containing compound to form the fluorinated acyl fluoride or derivative thereof.

Also disclosed herein are one or more compounds selected from:

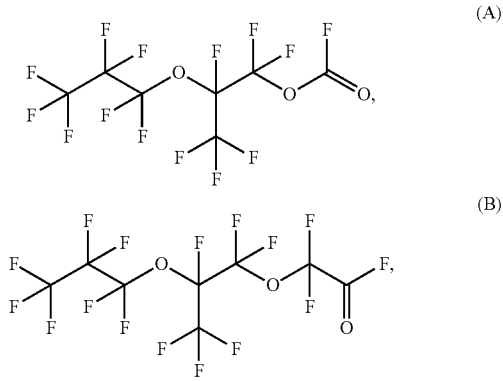

derivatives thereof, or combinations thereof.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range. All upper and lower limits can be combined in any combination to form ranges for the particular component or property for example.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Use of "first," "second," etc. in the description above and the claims that follow is not intended to necessarily indicate that the enumerated number of steps are present. For example, a "second" step is merely intended to differentiate from another step (such as a "first" step). Use of "first," "second," etc. in the description above and the claims that follow is also not necessarily intended to indicate that one comes earlier in time than the other.

When a group is present more than once in a formula described herein, each group is "independently" selected, whether specifically stated or not. For example, when more than one $R^1$ group is present in a formula, each $R^1$ group is independently selected. Furthermore, subgroups contained within these groups are also independently selected.

As used herein, the term "room temperature" refers to a temperature of about 20° C. to about 25° C. or about 22° C. to about 25° C.

Prior methods of oxidizing fluorinated compounds utilized Lewis Acids, for example antimony pentafluoride and titanium chloride. Such methods provided low yields that are not workable for the production of usable quantities. Later methods added increased pressure, but still did not obtain desired yields. Other methods obtained higher yields, but utilized very large amounts of reagents (e.g., KMnO$_4$) and produced large amounts of undesirable byproducts. Therefore, there remains a need for additional methods of converting fluorinated compounds to fluorinated acyl fluoride containing compounds or derivatives thereof.

Disclosed herein are methods of converting fluorinated compounds into fluorinated acyl fluoride compounds or derivatives thereof.

As used herein, "fluorinated" can refer to any compound that includes one or more than one fluorine (F) atoms bonded to a carbon. Fluorinated compounds can include partially fluorinated compounds and perfluorinated compounds. "Perfluorinated" means that all hydrogen atoms are replaced by fluorine atoms. For example, the term "perfluoromethyl" denotes an —CF$_3$ group. "partially fluorinated" means that at least one but not all hydrogen atoms are replaced by fluorine atoms. For example, a —CFH$_2$ group or a —CF$_2$H group are examples of partially fluorinated methyl residues.

Compounds that can be converted herein can include any functionalities and can represent virtually any classes of compounds. It should be noted however that the fluorinated compound being converted into a fluorinated acyl fluoride or derivative thereof does not include an acyl fluoride group and/or is not classified as an acyl fluoride compound. In some embodiments, the fluorinated compounds can be described by the functionality(ies) that they may include, for example, the fluorinated compounds can include olefin compounds or olefin containing compounds, ether containing compounds, and epoxide containing compounds for example. It should also be noted that a compound can be described by more than one class, for example a compound could be both an olefin containing compound and an ether containing compound. It should also be noted that fluorinated compounds to be converted herein can include any additional atoms, structures, or groups. Typically, the fluorinated compounds converted herein are fluorinated alkyl compounds that contain one or more than one functionality, such as those functionalities described herein.

As used herein "olefin containing compounds" or "olefin compounds" can refer to any compound that includes at least one carbon-carbon double bond. Olefin containing compounds can also be referred to as unsaturated compounds. Olefin containing compounds can include one or more than one carbon-carbon double bond.

As used herein "epoxide containing compound" can refer to any compound which contains an oxirane ring, which is a three-membered ring comprising two carbon atoms and an oxygen atom. Epoxide containing compounds can include one or more than one oxirane ring.

As used herein "ether containing compounds" can refer to any compound that includes at least one oxygen atom interposed between two carbon atoms (R—O—R). Ether containing compounds can include one or more than one R—O—R group. In some embodiments, ether containing compounds could be vinyl ether containing compounds. As used herein, "vinyl ether" means a moiety in a compound having two carbon atoms bonded to each other by a carboncarbon double bond, and at least one ether oxygen bonded to one of said double-bonded carbons atoms.

In some embodiments, fluorinated compounds to be converted herein can include fluorinated olefin compounds, for example. Such fluorinated olefin compounds can be linear, branched, cyclic or combinations thereof. A linear olefin is one that includes only a single chain of carbon (or other atoms), whereas a branched olefin is one that includes at least one pendant carbon group. In some embodiments, linear or branched fluorinated olefins can be converted herein. In some illustrative embodiments, the linear or branched fluorinated olefins can also include one or more ether groups. In some illustrative embodiments, the linear or branched fluorinated olefins can be perfluorinated linear or branched olefins.

In some specific illustrative embodiments, fluorinated linear olefin containing compounds can include from three (3) to twelve (12) carbon atoms, from four (4) to eight (8) carbon atoms, or from four (4) to six (6) carbon atoms. In some specific illustrative embodiments, fluorinated linear olefin containing compounds can include, for example partially fluorinated butene, perfluorinated butene, partially fluorinated pentene, perfluorinated pentene, or combinations thereof. In some specific illustrative embodiments, fluorinated linear olefin containing compounds can include, for example perfluorinated butene, perfluorinated pentene, or combinations thereof. Specific illustrative examples of perfluorinated vinyl-containing compounds can include C$_3$F$_7$—O—[CF(CF$_3$)—CF$_2$—O]$_x$—CF=CF$_2$ (with x=0 or 1), CF$_2$=CF—O—CF$_2$—CF$_2$—O—CF$_3$, CF$_3$—O—(CF$_2$)$_3$—O—CF=CF$_2$, CF$_2$=CF—O—CF$_2$—CF$_2$—O—CF$_2$—O—CF$_3$, CF$_2$=CF—O—(CF$_2$)$_x$—O—CF=CF$_2$ (with x=2 to 6) or similar compounds. Specific illustrative examples of partially fluorinated olefin containing compounds can include HCF$_2$—CF$_2$—CF$_2$—O—[CF(CF$_3$)—CF$_2$—O]$_x$—CF=CF$_2$ (with x=0 or 1) and CF$_3$—CH$_2$—O—CF=CF$_2$.

In some specific illustrative embodiments, fluorinated branched olefin containing compounds can include from four (4) to twelve (12) carbon atoms, from four (4) to ten (10) carbon atoms, or from four (4) to eight (8) carbon atoms. Specific illustrative examples of fluorinated branched olefin containing compounds can include C$_3$F$_7$OCF(CF$_3$)CF$_2$OCF=CF$_2$ (PPVE-2: 1,1,1,2,2,3,3-heptafluoro-3-({1,1,1,2,3,3-hexafluoro-3-[(trifluoroethenyl)oxy]propan-2-yl}oxy)propane) or similar compounds.

In some embodiments, cyclic fluorinated olefins can be converted herein. In some illustrative embodiments, the cyclic fluorinated olefins can include a single ring structure or a multi ring structure. In some illustrative embodiments, the cyclic fluorinated olefins can be a four (4) to eight (8) member carbon ring, or for example a four (4) to seven (7) member carbon ring. In some illustrative embodiments, the cyclic fluorinated olefin can be a perfluorinated cyclic olefin. In some specific illustrative embodiments, the fluorinated compound can include partially fluorinated cyclopentene or perfluorocyclopentene. In a specific illustrative embodiment, the fluorinated compound can include perfluorocyclopentene.

In some embodiments, fluorinated compounds to be converted herein can include epoxide containing compounds. Furthermore, a fluorinated compound can be converted into an epoxide containing fluorinated compound before it is converted into an acyl fluoride containing compound. As such, fluorinated epoxide containing compounds can be starting materials in disclosed methods or intermediates in the conversion of fluorinated compounds to acyl fluoride containing compounds. In some illustrative embodiments, an epoxide containing fluorinated compound can more specifically be described as an olefin epoxide containing fluorinated compound, or even more specifically a cyclic olefin epoxide containing fluorinated compound.

In some embodiments, fluorinated compounds to be converted herein can include fluorinated ether containing compounds. Fluorinated ether containing compounds can include one or more than one ether groups. In some embodiments, fluorinated ether containing compounds can include one ether groups, two ether groups, or more than two ether groups. Fluorinated ether containing compounds can also include one or more carbon-carbon double bonds (e.g., be an olefin containing compound as well), for example. In some specific examples, the fluorinated ether containing compound including one or more carbon-carbon double bonds could be a vinyl or allyl ether containing compound. In some embodiments, fluorinated ether containing compounds may be perfluorinated ether containing compounds, for example. More specifically, they could be perfluorinated ether olefin containing compounds, for example. Even more specifically, they could be perfluorinated vinyl or allyl ether containing compounds, for example. Specific illustrative examples of perfluorinated vinyl or allyl ether containing compounds can include $C_3F_7$—O—$[CF(CF_3)$—$CF_2$—$]_x$—CF=$CF_2$ (with x=0 or 1), $CF_2$=CF—O—$CF_3$, $CF_2$=CF—O—$CF_2$—$CF_2$—O—$CF_3$, $CF_3$—O—$(CF_2)_3$—O—CF=$CF_2$, $CF_2$=CF—O—$CF_2$—$CF_2$—O—$CF_2$—O—$CF_3$, $CF_2$=CF—$CF_2$—O—$CF_3$, $CF_2$=CF—$CF_2$—O—$CF_2$—$CF_2$—$CF_3$, $CF_2$=CF—$CF_2$—O—$CF_2$—$CF_2$—O—$CF_3$, $CF_2$=CF—$CF_2$—O—$CF_2$—$CF_2$—O—$CF_2$—O—$CF_3$, $CF_3$—O—$(CF_2)_3$—O—$CF_2$—CF=$CF_2$, $CF_2$=C—O—$(CF_2)_x$—O—CF=$CF_2$ (with x=2 to 6), $CF_2$=CF—$CF_2$—O—$(CF_2)_x$—O—$CF_2$—CF=$CF_2$ (with x=2 to 6), or similar compounds. Even more specifically, they could be perfluorinated vinyl ether containing compounds that include at least a second ether group, for example. Specific illustrative examples of partially fluorinated vinyl and allyl ether containing compounds can include $CF_3$—$CH_2$—O—CF=$CF_2$, $CF_3$—$CH_2$—O—$CF_2$—CF=$CF_2$, $HCF_2$—$CF_2$—$CF_2$—O—$CF(CF_3)$—$CF_2$—O—CF=$CF_2$ and $HCF_2$—$CF_2$—$CF_2$—O—$CF(CF_3)$—$CF_2$—O—$CF_2$—CF=$CF_2$.

Disclosed methods include reacting the fluorinated compound with a catalytic amount of at least one transition metal compound and an oxygen-containing compound. It should be noted that the transition metal compound and the oxygen-containing compound can be contacted with the fluorinated compound at the same time or at different times.

A "transition metal compound" can refer to any compound that includes one or more transition metals. Transition metals can include scandium (Sc), titanium (Ti), vanadium (V), chromium (Cr), manganese (Mn), iron (Fe), cobalt (Co), nickel (Ni), copper (Cu), yttrium (Y), zirconium (Zr), niobium (Nb), molybdenum (Mo), ruthenium (Ru), rhodium (Rh), palladium (Pd), silver (Ag), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu), hafnium (Hf), tantalum (Ta), tungsten (W), rhenium (Re), osmium (Os), iridium (Ir), platinum (Pt) and gold (Au). In some embodiments, transition metal compounds can include one or more transition metals that have or are in a relatively high oxidation state. Illustrative examples of such transition metals that can be utilized in transition metal compounds can include Ti, V, Cr, Mn, Fe, Co, Ni, Zr, Nb, Mo, Ru, Rh, Pd, Hf, Ta, W, Re, Os, Ir, and Pt. Illustrative examples of such transition metals that can be utilized in transition metal compounds can include V, Mo, W, and Ti for example.

Transition metal compounds that can be utilized in methods can be in various different forms. For example the transition metal compound can be an oxide, a spinel compound, an oxoperoxo metal compound, an oxoperoxo metal complex with organic complexing agents, or any combination thereof.

In some embodiments, the transition metal compounds can be oxides including the one or more transition metals. In some embodiments, transition metal compounds can be oxides of a transition metal having a relatively high oxidation state. Transition metal oxides can include metals other than transition metals therein. In some embodiments, the transition metal compound can be a transition metal oxide(s), for example oxides of one or more of Ti, V, Cr, Mn, Fe, Co, Ni, Zr, Nb, Mo, Ru, Rh, Pd, Hf, Ta, W, Re, Os, Ir, and Pt; or oxides of V. In some embodiments, a transition metal compound can include vanadium oxide ($V_2O_5$) for example. In some embodiments an illustrative transition metal oxide can include potassium permanganate ($KMnO_4$), for example. Transition metal oxides can be used in powder form, granular form, or any other convenient form.

In some embodiments, the transition metal compounds can be spinel compounds. Spinel compounds have the general formula $A^{2+}B^{3+}_2O^{2-}_4$, where A and B are two metal atoms. The two metal atoms (A and B) may, but need not be different metals. For example, the two metals may be the same metal, but have different oxidation states (for example, both A and B may be iron (Fe), where A is $Fe^{2+}$ and B is $Fe^{3+}$. In some embodiments, both A and B are transition metals (as listed above) and in other embodiments, only one of A or B are transition metals. In some embodiments A and B can be selected from Mn, Fe, Cr, Co, Zn, Fe, Ni, aluminum (Al), and magnesium (Mg). Some specific, illustrative spinel compounds can include $Mn_3O_4$, $FeCr_2O_4$, $CoAl_2O_4$, $Co_3O_4$, $ZnAl_2O_3$, $Fe_3O_4$, $CoFe_2O_4$, $NiFe_2O_4$, and $MgFe_2O_4$.

In some embodiments, the transition metal compounds can be oxoperoxo metal compounds. An example of an oxoperoxo metal compound includes $MoO(O_2)_2*nH_2O$. Further specific regarding oxoperoxo compounds can be found in *Appl. Catal., A*, 2007, 327, 205-21; the disclosure of which is incorporated herein by reference thereto. In some embodiments, the transition metal compounds can be oxoperoxo metal complexes with organic complexing agents. In some embodiments, illustrative oxoperoxo metal complexes with organic complexing agents can include nitrogen atoms (N), oxygen atoms (O), or combinations thereof as coordinating sites. Illustrative examples of oxoperoxo metal complexes with organic complexing agents include $MoO(O_2)_2*4,4'$-bipyridine, $MoO(O_2)_2*4$-methylpyridinium N-oxide*$H_2O$, and $VO(O_2)$ (pyrazine-2-carboxylate)*$2H_2O$. Further details regarding the molybdenum bipyridine compound can be found in *Appl. Catal., A*, 2007, 327, 205-21, the molybdenum methylpyridinium compund can be found in *Polyhedron* 2009, 28, 3929-3934, and the vanadium compound can be found in *J. Am. Chem. Soc.* 1983, 105, 3101-3110; the disclosures of which are incorporated herein by reference thereto. Illustrative specific metals that can be utilized in oxoperoxo metal compounds an include V, Mo and W for example.

The transition metal compound is used in a catalytic amount. In some embodiments, a catalytic amount of a transition metal compound is not greater than 20 mol %, not greater than 10 mol %, not greater than 8 mol %, or not greater than 5 mol % of the transition metal compound based on the total mols of the fluorinated compound being converted. In some embodiments, a catalytic amount of a transition metal compound is not less than 1 mol % based on the total mols of the fluorinated compound being converted.

Disclosed methods include reacting the fluorinated compound with a catalytic amount of at least one transition metal compound and an oxygen-containing compound. The oxygen-containing compound can be a gas at reaction temperature (or room temperature, or both), a liquid at reaction temperature (or room temperature or both), a solid at reaction temperature (or room temperature or both), or a combination thereof (e.g., more than one oxygen-containing compound). In some embodiments, the oxygen-containing compound can be an oxygen-containing gas, for example. The oxygen-containing compound can be provided to the atmosphere of the reaction or to the reaction mixture. In embodiments where an oxygen-containing gas is being utilized, any gas that includes oxygen atoms can be utilized. In some embodiments, an oxygen-containing gas can include oxygen ($O_2$), water ($H_2O$), hydrogen peroxide ($H_2O_2$), ozone ($O_3$), nitrous oxide ($N_2O$), or combinations thereof. In some embodiments, oxygen gas (O₂) can be utilized. In some embodiments, the amount of moles of the oxygen-containing compound to the amount of moles of the fluorinated compound can be not less than 1 mole oxygen-containing compound to 1 mole fluorinated compound (e.g., ≥1:1), and not greater than 10 moles oxygen-containing compound to 1 mole fluorinated compound (e.g., ≤10:1).

Various reaction conditions can be controlled and/or modified when carrying out various disclosed methods. Examples of such reaction conditions can include, for example temperature and pressure. In some embodiments, methods can be carried out under an increased temperature (e.g. not less than room temperature, about 25° C.), for example. In some embodiments, reacting a fluorinated compound with a transition metal compound and an oxygen-containing compound can be carried out at temperatures of not less than 50° C., not less than 65° C., or not less than 70° C., for example. In some embodiments, reacting a fluorinated compound with a transition metal compound and an oxygen-containing compound can be carried out at temperatures of not greater than 650° C., not greater than 500° C., not greater than 250° C., not greater than 100° C., or not greater than 95° C. Methods that are converting cyclic olefins may advantageously utilize higher temperatures, e.g., temperatures of not less than 100° C., even not less than 400° C., or even not less than 440° C. In some embodiments, methods can be carried out under an increased pressure (e.g., greater than atmospheric temperature, about 1 bar), for example. In some embodiments, disclosed methods can be carried out at pressures not greater than 20 bar (e.g., ≤20 bar), or in some embodiments not greater than 5 bar (e.g., ≤5 bar). In some embodiments, disclosed methods can be carried out at pressures not less than 1 bar (e.g., ≥1 bar).

Disclosed methods can be carried out using known synthesis methods, processes, reaction vessels and other standard equipment. Disclosed methods can be carried out in a batch mode, in a continuous mode (e.g., a flow reactor), or a combination thereof. Disclosed methods can be carried out in the bulk or in a solvent. Illustrative solvents can include non-reactive solvents such as inert fluorinated (either partially fluorinated or perfluorinated) solvents. In some embodiments, supercritical liquids or gases can be utilized, for example supercritical carbon dioxide (scCO₂).

Disclosed methods convert fluorinated compounds into fluorinated acyl fluoride or derivatives thereof. "Acyl fluoride" can refer to an organic acid group in with the —OH of a carboxylic acid has been replaced with a fluorine atom (RC(O)F). Acyl fluoride containing compounds or simply acyl fluorides then refer to compounds that include an acyl fluoride group. Methods disclosed herein convert fluorinated compounds into fluorinated acyl fluorides. A fluorinated acyl fluoride generally includes more fluorine atoms than the one in the acyl fluoride group. Acyl fluoride containing compounds may be useful because they can typically relatively easily be reacted with other compounds. "Acyl fluoride derivative" or a derivative of acyl fluoride can refer to an acyl fluoride that has been subjected to hydrolysis, esterification, or ammonolysis for example. The acyl fluoride derivatives are therefore carboxylic acids (once subjected to hydrolysis), esters (once esterified), or amides or nitriles (once subjected to ammonolysis). It should be noted that any methods of derivatizing, or further reacting specific acyl fluorides, (e.g., those discussed below with regard to the reaction Schemes) can be utilized to derivatize or react any acyl fluorides, not only the particular acyl fluorides that are mentioned in the reaction schemes. Fluorinated acyl fluorides formed using disclosed methods can also include various other functional groups, depending, at least in part, on the starting fluorinated compound, for example.

Specific illustrative examples of fluorinated acyl fluorides that can be formed using disclosed methods include compounds A and B below.

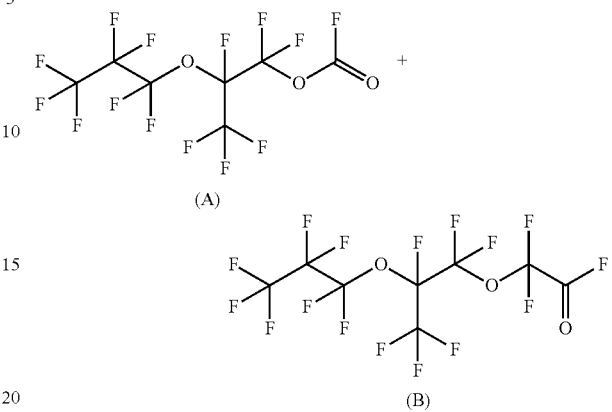

Compound A, 1,1,2,3,3,3-hexafluoro-2-(heptafluoropropoxy)propyl fluorocarbonate and compound B, 2,2-difluoro-2-(1,1,2,3,3,3-hexafluoro-2-(perfluoropropoxy)propoxy)acetyl fluoride can be formed by starting with a perfluorinated vinyl ether compound, specifically, 1,1,1,2,2,3,3-heptafluoro-3-({1,1,1,2,3,3-hexafluoro-3-[(trifluoroethenyl)oxy]propan-2-yl}oxy)propane, which is often referred to as PPVE-2. Structurally, this reaction is depicted below in Scheme 1

Scheme 1

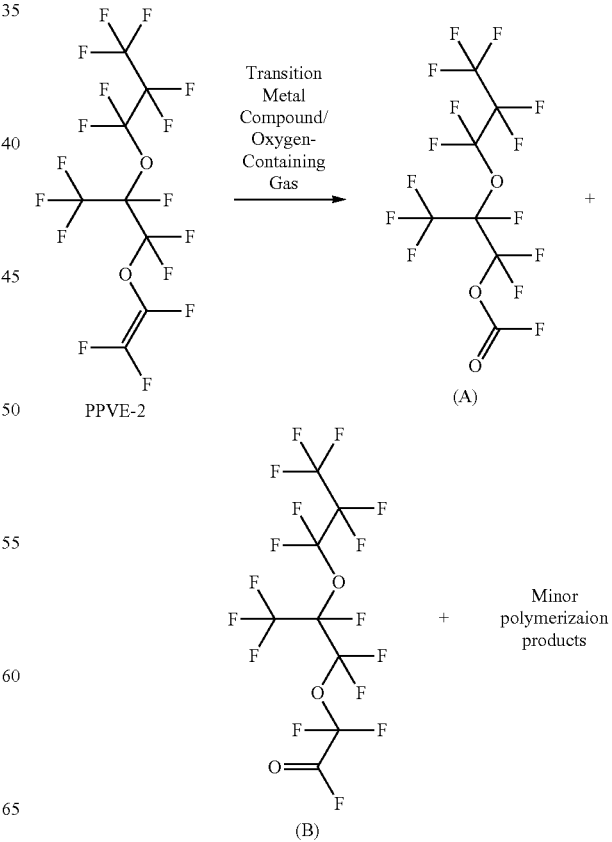

Acyl fluorides, including compounds A and B above for example, can be further modified or reacted once obtained to obtain derivatives of the fluorinated acyl fluoride compounds. For example, they can be subjected to hydrolysis or esterification for example. Scheme 2 below shows the hydrolysis of compounds A and B.

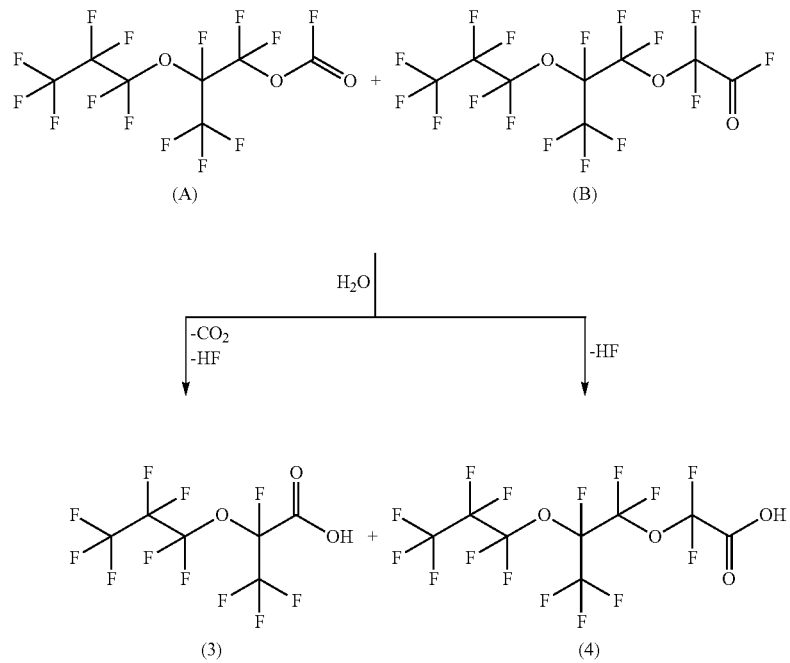

Acyl fluorides, of which compounds A and B are examples can also be subjected to esterification for example. Scheme 3 below shows the esterification of compounds A and B with methanol, as an example.

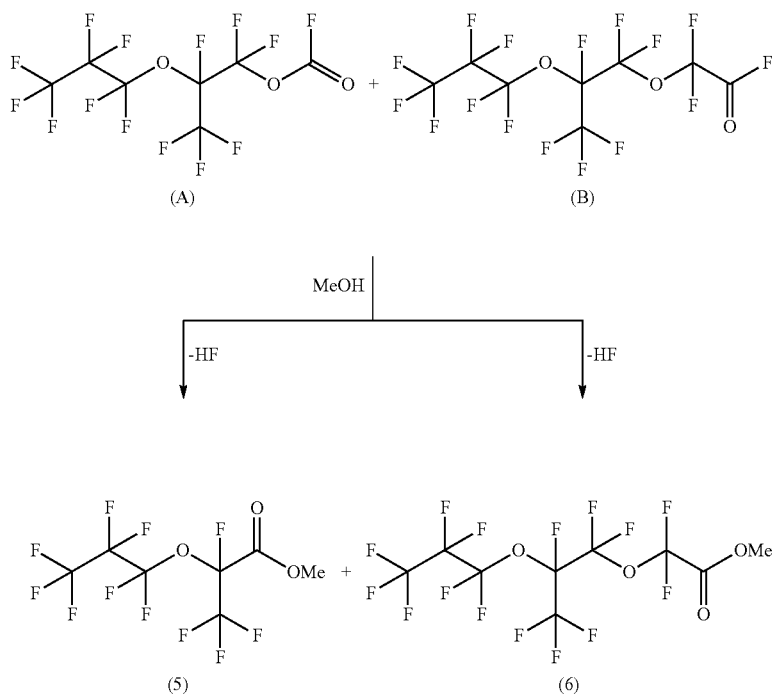

Fluorinated acyl fluorides that can be made from fluorinated cyclic olefins are illustrated by converting perfluorocyclopentene (7). This reaction is depicted in Scheme 4 below. Scheme 4 depicts the conversion of the perfluorocyclpentene (7) via oxidation (with transition metal compound and oxygen-containing gas) to the acyl fluoride, 2,2,3,3,4,4-hexafluoropentanedioyl difluoride (8).

Scheme 4

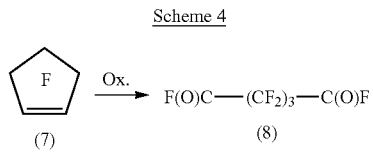

Acyl fluorides formed from fluorinated cyclic olefins such as perfluorocyclpentene (7) for example can also be further reacted or derivatized. Various reactions can be carried out including for example, converting the acyl fluoride to a chain transfer agent, or reacting the acyl fluoride with various other fluoride reagents to form compounds, including for example vinyl- or allyl-ethers, bisolefins, or nitrile containing compounds. Another specific illustrative example of a reaction that may be carried out with acyl fluorides formed herein include reacting the acyl fluoride with hexafluoropropene oxide (HFPO), or perfluoro allyl fluorosulfate to form vinyl- or allyl-ethers.

Schemes 5a, 5b, 5c and 5d show possible reaction schemes, specifically conversion of the acyl fluoride into a chain transfer agent, compound 10 (Scheme 5a); reaction of the acyl fluoride with HFPO (Scheme 5b), reaction to a nitrile (Scheme 5c) and reaction with a fluorosulfate (Scheme 5d) for illustrative compound 9, 2,2,3,3,4,4-hexafluoropentanedioyl difluoride.

Scheme 5a

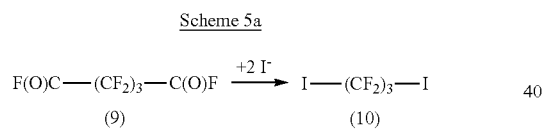

Scheme 5b

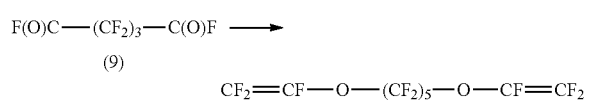

Scheme 5c

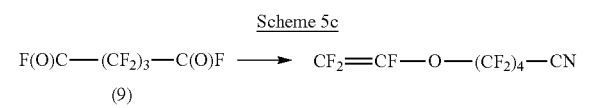

Scheme 5d

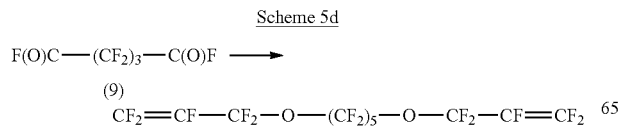

Fluorinated acyl fluorides that can be made from fluorinated linear olefins are illustrated by converting perfluoropent-2-ene, compound 10, via oxidation (with transition metal compound and oxygen-containing gas) to acyl fluorides, compounds 11 and 12. This reaction is depicted in Scheme 6 below.

Scheme 6

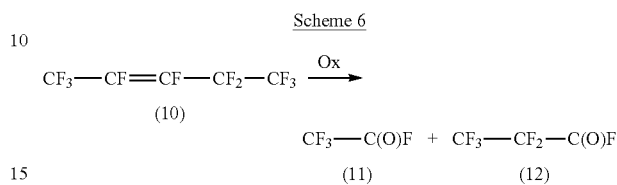

Acyl fluorides formed from fluorinated linear olefins such as perfluoropent-2-ene (10) for example can also be further reacted or derivatized. Various reactions can be carried out including for example, reacting the acyl fluoride with various other fluoride reagents to form compounds, including for example vinyl- or allyl-ethers, bisolefins, or nitrile containing compounds. Another specific illustrative example of a reaction that may be carried out with acyl fluorides formed herein include reacting the acyl fluoride with hexafluoropropene oxide (HFPO), or perfluoro allyl fluorosulfate to form vinyl- or allyl-ethers. Scheme 7a shows the reaction of the mixture of compounds 11 and 12 with HFPO and Scheme 7b with a perfluoro allyl fluorosulfate.

Scheme 7a

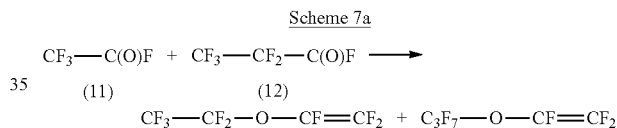

Scheme 7b

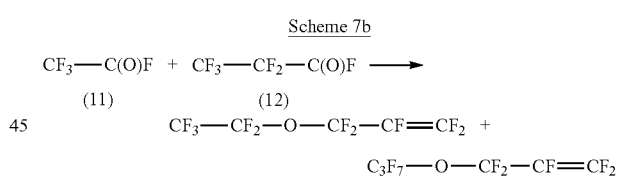

Reaction schemes similar to those seen in Schemes 6, 7a and 7b can also be illustrated by the conversion of another fluorinated linear olefin perfluoropent-1-ene, compound 13, via oxidation (with transition metal compound and oxygen-containing gas) to the acyl fluorides, compounds 14 and 15. This reaction is depicted in Scheme 8 below.

Scheme 8

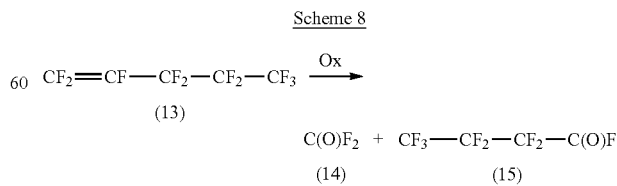

Acyl fluorides formed from fluorinated linear olefins such as perfluoropent-1-ene (13) for example can also be further reacted or derivatized. Various reactions can be carried out including for example, reacting the acyl fluoride with various other fluoride reagents to form compounds, such as for example vinyl- or allyl-ethers, bisolefins, or nitrile containing compounds. Another specific illustrative example of a reaction that may be carried out with acyl fluorides formed herein include reacting the acyl fluoride with hexafluoropropene oxide (HFPO), or perfluoro allyl fluorosulfate to form vinyl- or allyl-ethers. Scheme 9a shows the reaction of the mixture of compounds 14 and 15 with HFPO and Scheme 9b with a perfluoro allyl fluorosulfate Scheme 9a

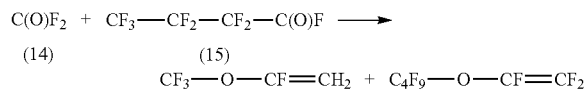

Scheme 9b

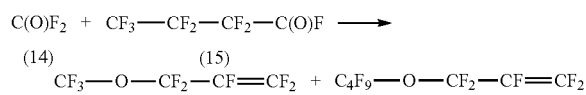

Additional specific compounds that could be formed by converting perfluoro linear olefins into acyl fluorides using disclosed methods and then further reacting the acyl fluorides, derivatizing them, or both can include, for example $CF_3—O—CF=CF_2$, $C_2F_5—O—CF=CF_2$, $C_3F_7—O—CF=CF_2$, $C_4F_9—O—CF=CF_2$, $CF_3—O—CF_2—CF=CF_2$, $C_2F_5—O—CF_2—CF=CF_2$, $C_3F_7—O—CF_2—CF=CF_2$, $C_4F_9—O—CF_2—CF=CF_2$, $CF_2=CF—O—(CF_2)_5—O—CF=CF_2$, $CF_2=CF—CF_2—O—(CF_2)_5—O—CF_2—CF=CF_2$, $CF_2=CF—O—(CF_2)_4—CN$, and $X—(CF_2)_3—X$ (with X independently selected from I and Br) for example.

The following is a summary of particular, specific embodiments of the present disclosure.

Some illustrative embodiments include methods of converting a fluorinated compound into a fluorinated acyl fluoride or derivative thereof, the method comprising: reacting the fluorinated compound with a catalytic amount of at least one transition metal compound and an oxygen-containing compound to form the fluorinated acyl fluoride or derivative thereof.

In the following paragraph "such methods" refer to the illustrative method immediately above as well as any other methods disclosed in this paragraph. Such methods, wherein the fluorinated compound comprises at least one epoxide group. Such methods, wherein the fluorinated compound comprises at least one ether group. Such methods, wherein the fluorinated compound is a fluorinated olefin containing compound. Such methods, wherein the fluorinated compound has from three (3) to twelve (12) carbons. Such methods, wherein the fluorinated compound has from four (4) to eight (8) carbon atoms. Such methods, wherein the fluorinated compound is a partially fluorinated four carbon chain compound, partially fluorinated five carbon chain compound, partially fluorinated six carbon chain compound, perfluorinated four carbon chain compound, perfluorinated five carbon chain compound, perfluorinated six carbon chain compound, or combinations thereof. Such methods, wherein the fluorinated compound is a perfluorinated vinyl ether compound. Such methods, wherein the fluorinated compound is a cyclic fluorinated olefin. Such methods, wherein the fluorinated olefin has from five (5) to ten (10) carbons. Such methods, wherein the fluorinated olefin is partially fluorinated cylcopentene, perfluorocyclopentene, or combinations thereof. Such methods, wherein the transition metal compound comprises Ti, V, Cr, Mn, Fe, Co, Ni, Zr, Nb, Mo, Ru, Rh, Pd, Hf, Ta, W, Re, Os, Ir, Pt, or combinations thereof. Such methods, wherein the transition metal compound comprises vanadium oxide ($V_2O_5$), molybdenum oxide ($MoO_3$), or combinations thereof. Such methods, wherein the transition metal compound comprises vanadium oxide ($V_2O_5$). Such methods, wherein the catalytic amount of the transition metal compound is not greater than 20 mol % transition metal oxide based on the total mols of the olefin. Such methods, wherein the catalytic amount of the transition metal compound is not greater than 10 mol % transition metal oxide based on the total mols of the olefin. Such methods, wherein the catalytic amount of the transition metal compound is not greater than 8 mol % transition metal oxide based on the total mols of the olefin. Such methods, wherein the catalytic amount of the transition metal compound is not greater than 5 mol % transition metal compound based on the total mols of the olefin. Such methods, wherein the catalytic amount of the transition metal compound is about 1 mol % to about 5 mol % transition metal compound based on the total mols of the olefin. Such methods, wherein the oxygen-containing compound comprises an oxygen-containing gas. Such methods, wherein the oxygen-containing gas comprises oxygen ($O_2$), water ($H_2O$), hydrogen peroxide ($H_2O_2$), ozone ($O_3$), nitrous oxide ($N_2O$), or combinations thereof. Such methods, wherein the oxygen-containing gas comprises $O_2$. Such methods, wherein the reaction is carried out at a temperature of not less than about 50° C. Such methods, wherein the reaction is carried out at a temperature from about 50° C. to about 650° C. Such methods, wherein the reaction is carried out at a temperature from about 70° C. to about 500° C. Such methods, wherein the fluorinated acyl fluoride is

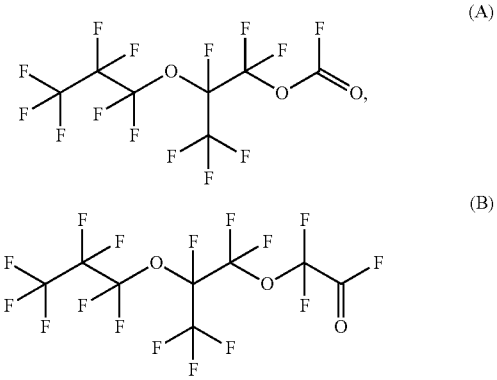

derivatives thereof, or combinations thereof. Such methods further comprising hydrolyzing the fluorinated acyl fluoride to form a derivative of the fluorinated acyl fluoride. Such methods, wherein the hydrolysis occurs at temperatures greater than room temperature. Such methods further comprising esterifying the fluorinated acyl fluoride. Such methods, wherein esterifying occurs by reacting the fluorinated acyl fluoride with an alcohol. Such methods, wherein the alcohol is selected from methanol, ethanol, propanol, or combinations thereof. Such methods further comprising reacting the fluorinated acyl fluoride with an iodine containing compound to form a chain transfer agent. Such methods further comprising reacting the fluorinated acyl fluoride with other fluoride containing reagents to form vinyl- or allyl-ethers, bisolefins, or nitrile containing compounds. Such methods further comprising reacting the fluorinated acyl fluoride with hexafluoropropene oxide (HFPO), a perfluoro allyl fluorosulfate, or combinations thereof to form vinyl-ethers, allyl-ethers, or combinations thereof. Such methods wherein the derivative of the acyl fluoride compound comprises: $CF_3$—O—$CF$=$CF_2$, $C_2F_5$—O—$CF$=$CF_2$, $C_3F_7$—O—$CF$=$CF_2$, $C_4F_9$—O—$CF$=$CF_2$, $CF_3$—O—$CF_2$—$CF$=$CF_2$, $C_2F_5$—O—$CF_2$—$CF$=$CF_2$, $C_3F_7$—O—$CF_2$—$CF$=$CF_2$, $C_4F_9$—O—$CF_2$—$CF$=$CF_2$, $CF_2$=$CF$—O—$(CF_2)_5$—O—$CF$=$CF_2$, $CF_2$=$CF$—$CF_2$—O—$(CF_2)_5$—O—$CF_2$—$CF$=$CF_2$, $CF_2$=$CF$—O—$(CF_2)_4$—CN, X—$(CF_2)_3$—X (with X independently selected from I and Br), or combinations thereof. Such methods, wherein the fluorinated compound converted into an acyl fluoride compound comprises 1,1,1,2,2,3,3-heptafluoro-3-({1,1,1,2,3,3-hexafluoro-3-[(trifluoroethenypoxy]propan-2-yl}oxy)propane (PPVE-2).

Additional illustrative embodiments can include one or more compounds selected from:

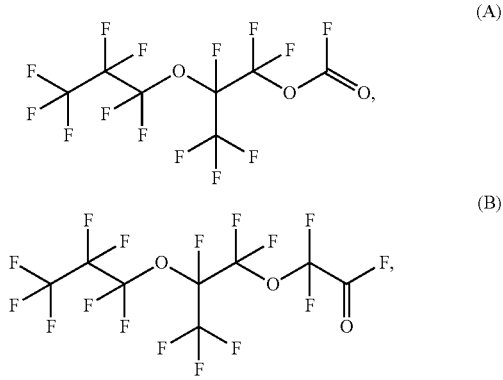

derivatives thereof, or combinations thereof.

Objects and advantages of this disclosure may be further illustrated by the following non-limiting examples, but the particular materials and amounts thereof recited in these examples, as well as other conditions and details should not be construed to limit this disclosure in any way.

EXAMPLES

Unless otherwise noted, all chemicals used in the examples can be obtained from Sigma-Aldrich Corp. (Saint Louis, Mo.).

The following abbreviations are used in this section: mol=moles, mmol=millimoles, mol %=mole percent, h=hours, NMR=nuclear magnetic resonance, mmHg=millimeters of mercury, Hz=hertz

TABLE 1

| Materials used in examples | |
|---|---|
| Material | Description |
| PPVE-2 | Perfluoro(5-methyl-3,6-dioxanon-1-ene), available from abcr GmbH, Germany |
| $V_2O_5$ | Powder, available from Sigma-Aldrich |
| c-$C_5F_8$ | Perfluorocyclopentene, available from abcr GmbH, Germany |
| Methanol | Available from Sigma-Aldrich |

TABLE 1-continued

| Materials used in examples | |
|---|---|
| Material | Description |
| $MoO(O_2)_2$* 4,4'-bipyridine | May be synthesized as described in Appl. Catal. A, 2007, 327, 205-221. |
| $MoO(O_2)_2$* 4-methylpyridinium N-oxide * $H_2O$ | May be synthesized as described in Polyhedron, 2009, 28, 3929-3934. |

Characterization

NMR spectra were obtained on a JEOL ECX 400 spectrometer operating at 400 MHz for $^1H$ (TMS), 376 MHz for $^{19}F$ ($CFCl_3$) and 100 MHz for $^{13}C$ (TMS) at 22° C. The yields were obtained by the weighed quantity of sample and the determined molar/weight ratio.

Identification of 1,1,2,3,3,3-hexafluoro-2-(heptafluoropropoxy)propyl fluorocarbonate (Product A) by NMR: $^{19}F$ NMR (376 MHz, neat, δ): −14.4 (s, 1F, COF), −82.0 (d, $^3J_{FF}$=9 Hz, 3F, $CF_3$), −83.2 (m, 2F, $CF_2O$), −83.6 (bs, 3F, $CF_3$), −89.8 (dm, $^3J_{FF}$=7 Hz, 2F, $CF_2O$), −131.6 (s, 2F, $CF_2$), −146.5 (t, $^3J_{FF}$=22 Hz, 1F, CF).

Identification of 2,2-difluoro-2-(1,1,2,3,3,3-hexafluoro-2-(perfluoropropoxy)propoxy)acetyl fluoride (Product B) by NMR: $^{19}F$ NMR (376 MHz, neat, δ): +10.9 (s, 1F, COF), −78.4 (t, $^4J_{FF}$=12, 2F, $CF_2$), −82.0 (d, $^3J_{FF}$=7 Hz, 3F, $CF_3$), −83.1 (dm, $^2J_{FF}$=54 Hz, 2F, $CF_2O$), −83.6 (bs, 3F, $CF_3$), −84.3 (dm, $^2J_{FF}$=41 Hz, 2F, $CF_2O$), −131.5 (s, 2F, $CF_2$), −146.7 (t, $^3J_{FF}$=22 Hz, 1F, CF).

Examples 1 Through 5

For Example 1 (EX-1), under anhydrous conditions, PPVE-2 (101 g, 0.23 mol, 60 mL) and $V_2O_5$ (2.2 g, 12.1 mmol, 5 mol %), were added to a three-necked 100 mL flask equipped with bubbler, thermometer, and reflux condenser. The reaction mixture was heated to 80° C. and oxygen was passed through. Thereby, an exothermic effect occurred and the temperature raised to 95° C. At this temperature, oxygen was further added for 3.5 h. After decreasing to 77° C., oxygen was additionally bubbled for 30 min. Afterwards, all liquids were condensed into a trap cooled to −90° C. (anhydrous conditions, 16 mmHg). NMR analysis of the 83.9 g of product obtained indicated a mixture of Product A (20.7 g, 0.052 mol, yield 23%) and Product B (63.2 g, 0.14 mol, yield 61%).

For Examples 2 (EX-2) through 5 (EX-5), the same procedure was followed as for Example 1, but with varying mol % of $V_2O_5$, as indicated in Table 2. The ratio of Product A to Product B for Examples 2 through 5 is indicated in Table 2.

Comparatives 1 and 2

For Comparatives 1 (C-1) and 2 (C-2), the same procedure was followed as described for EX-1, except that the temperature of the reaction mixture was varied as indicated in Table 2. As indicated in Table 2, there was no conversion of PPVE-2 observed by $^{19}F$ NMR for C-1 or C-2.

Examples 6 and 7

For Examples 6 (EX-6) and 7 (EX-7), the same procedure was followed as described for EX-2, except that, instead of 10 mol % of $V_2O_5$, 10 mol % of $MoO(O_2)_2$*4,4'-bipyridine was used for EX-6, and 10 mol % of $MoO(O_2)_2$*4-methylpyridinium N-oxide*$H_2O$ was used for EX-7. Conversion of PPVE-2 for EX-6 through EX-7 is provided in Table 2.

TABLE 2

| | | | | | | Ratio of Product A/ Product B |
|---|---|---|---|---|---|---|
| | | | (% Conversion by $^{19}$F NMR) | | | |
| Example or Comparative | Catalyst | Catalyst [mol %] | $T_{reaction}$ [° C.] | $t_{reaction}$ [h] | % Conversion of PPVE-2$^a$ | [mol %/ mol %] |
| C-1 | $V_2O_5$ | 20 | r.t. | 2.5 | — | —/— |
| C-2 | $V_2O_5$ | 20 | 65 | 2.5 | — | —/— |
| EX-1 | $V_2O_5$ | 20 | 73-95 | 2.5 | 100 | 29.9/70.1 |
| EX-2 | $V_2O_5$ | 10 | 73-92 | 12 | 100 | 22.7/77.3 |
| EX-3 | $V_2O_5$ | 5 | 73-92 | 4 | 100 | 24.7/75.3 |
| EX-4 | $V_2O_5$ | 0.5 | 85 | 3.5 | 65 | 25/75 |
| EX-5 | $V_2O_5$ | 0.1 | 82 | 3 | 35 | 25/75 |
| EX-6 | $MoO(O_2)_2$ * 4,4'-bipyridine | 10 | 80-84 | 16 | 12 | —/10 |
| EX-7 | $MoO(O_2)_2$ * 4-methylpyridinium N-oxide * $H_2O$ | 10 | 80-84 | 13 | 13 | —/1 |

Example 8 (EX-8)

The product obtained from Example 1 was reacted with water at 45° C., resulting in a mixture of 2,3,3,3-tetrafluoro-2-(heptafluoropropoxy)propanoic acid and difluoro[1,1,2,3,3,3-hexafluoro-2-(heptafluoropropoxy)propoxy]acetic acid (confirmed by NMR).

Example 9 (EX-9)

The product obtained from Example 1 was reacted with MeOH at 50° C., resulting in a mixture of methyl 2,3,3,3-tetrafluoro-2-(heptafluoropropoxy)propanoate and methyl difluoro[1,1,2,3,3,3-hexafluoro-2-(heptafluoropropoxy)propoxy]acetate (confirmed by NMR).

Thus, embodiments of methods for converting fluorinated compounds are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

Exemplary embodiments include the following:

Embodiment 1

A method of converting a fluorinated compound into a fluorinated acyl fluoride or derivative thereof, the method comprising:
reacting the fluorinated compound with a catalytic amount of at least one transition metal compound and an oxygen-containing compound to form the fluorinated acyl fluoride or derivative thereof.

Embodiment 2

The method according to embodiment 1, wherein the fluorinated compound comprises at least one epoxide group.

Embodiment 3

The method according to any one of embodiments 1 to 2, wherein the fluorinated compound comprises at least one ether group.

Embodiment 4

The method according to any one of embodiments 1 to 3, wherein the fluorinated compound is a fluorinated olefin containing compound.

Embodiment 5

The method according to any one of embodiments 1 to 4, wherein the fluorinated compound has from three (3) to twelve (12) carbons.

Embodiment 6

The method according to any one of embodiments 1 to 5, wherein the fluorinated compound has from four (4) to eight (8) carbon atoms.

Embodiment 7

The method according to any one of embodiments 1 to 6, wherein the fluorinated compound is a partially fluorinated four carbon chain compound, partially fluorinated five carbon chain compound, partially fluorinated six carbon chain compound, perfluorinated four carbon chain compound, perfluorinated five carbon chain compound, perfluorinated six carbon chain compound, or combinations thereof.

Embodiment 8

The method according to any one of embodiments 1 to 7, wherein the fluorinated compound is a perfluorinated vinyl ether compound.

Embodiment 9

The method according to any one of embodiments 1 to 8, wherein the fluorinated compound is a cyclic fluorinated olefin.

Embodiment 10

The method according to embodiment 9, wherein the fluorinated olefin has from five (5) to ten (10) carbons.

Embodiment 11

The method according to any of embodiments 9 or 10, wherein the fluorinated olefin is partially fluorinated cylcopentene, perfluorocyclopentene, or combinations thereof.

Embodiment 12

The method according to any one of embodiments 1 to 11, wherein the transition metal compound comprises Ti, V, Cr, Mn, Fe, Co, Ni, Zr, Nb, Mo, Ru, Rh, Pd, Hf, Ta, W, Re, Os, Ir, Pt, or combinations thereof.

Embodiment 13

The method according to any one of embodiments 1 to 12, wherein the transition metal compound comprises vanadium oxide ($V_2O_5$), molybdenum oxide ($MoO_3$), or combinations thereof.

Embodiment 14

The method according to any one of embodiments 1 to 13, wherein the transition metal compound comprises vanadium oxide ($V_2O_5$).

Embodiment 15

The method according to any one of embodiments 1 to 14, wherein the catalytic amount of the transition metal compound is not greater than 20 mol % transition metal oxide based on the total mols of the olefin.

Embodiment 16

The method according to any one of embodiments 1 to 15, wherein the catalytic amount of the transition metal compound is not greater than 10 mol % transition metal oxide based on the total mols of the olefin.

Embodiment 17

The method according to any one of embodiments 1 to 16, wherein the catalytic amount of the transition metal compound is not greater than 8 mol % transition metal oxide based on the total mols of the olefin.

Embodiment 18

The method according to any one of embodiments 1 to 17, wherein the catalytic amount of the transition metal compound is not greater than 5 mol % transition metal compound based on the total mols of the olefin.

Embodiment 19

The method according to any one of embodiments 1 to 18, wherein the catalytic amount of the transition metal compound is about 1 mol % to about 5 mol % transition metal compound based on the total mols of the olefin.

Embodiment 20

The method according to any one of embodiments 1 to 19, wherein the oxygen-containing compound comprises an oxygen-containing gas.

Embodiment 21

The method according to embodiment 20, wherein the oxygen-containing gas comprises oxygen ($O_2$), water ($H_2O$), hydrogen peroxide ($H_2O_2$), ozone ($O_3$), nitrous oxide ($N_2O$), or combinations thereof.

Embodiment 22

The method according to any one of embodiments 20 to 21, wherein the oxygen-containing gas comprises $O_2$.

Embodiment 23

The method according to any one of embodiments 1 to 22, wherein the reaction is carried out at a temperature of not less than about 50° C.

Embodiment 24

The method according to any one of embodiments 1 to 23, wherein the reaction is carried out at a temperature from about 50° C. to about 650° C.

Embodiment 25

The method according to any one of embodiments 1 to 26, wherein the reaction is carried out at a temperature from about 70° C. to about 500° C.

Embodiment 26

The method according to any one of embodiments 1 to 25, wherein the fluorinated acyl fluoride is

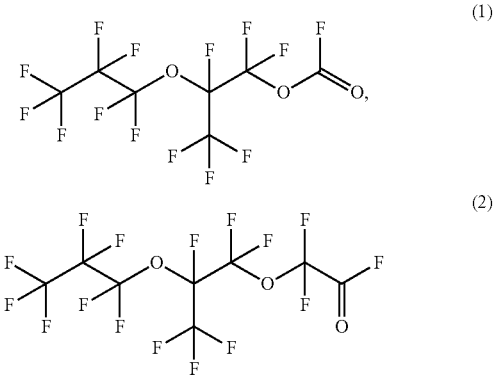

derivatives thereof, or combinations thereof.

Embodiment 27

The method according to any one of embodiments 1 to 26 further comprising hydrolyzing the fluorinated acyl fluoride to form a derivative of the fluorinated acyl fluoride.

Embodiment 28

The method according to embodiment 27, wherein the hydrolysis occurs at temperatures greater than room temperature.

Embodiment 29

The method according to any of embodiments 1 to 26 further comprising esterifying the fluorinated acyl fluoride.

Embodiment 30

The method according to embodiment 29, wherein esterifying occurs by reacting the fluorinated acyl fluoride with an alcohol.

Embodiment 31

The method according to embodiment 30, wherein the alcohol is selected from methanol, ethanol, propanol, or combinations thereof.

Embodiment 32

The method according to any one of embodiments 1 to 26 further comprising reacting the fluorinated acyl fluoride with an iodine containing compound to form a chain transfer agent.

Embodiment 33

The method according to any one of embodiments 1 to 26 further comprising reacting the fluorinated acyl fluoride with other fluoride containing reagents to form vinyl- or allyl-ethers, bisolefins, or nitrile containing compounds.

Embodiment 34

The method according to any one of embodiments 1 to 26 further comprising reacting the fluorinated acyl fluoride with hexafluoropropene oxide (HFPO), a perfluoro allyl fluorosulfate, or combinations thereof to form vinyl-ethers, allyl-ethers, or combinations thereof.

Embodiment 35

The methods according to any one of embodiments 24 to 34, wherein the derivative of the acyl fluoride compound comprises: $CF_3$—O—$CF$=$CF_2$, $C_2F_5$—O—$CF$=$CF_2$, $C_3F_7$—O—$CF$=$CF_2$, $C_4F_9$—O—$CF$=$CF_2$, $CF_3$—O—$CF_2$—$CF$=$CF_2$, $C_2F_5$—O—$CF_2$—$CF$=$CF_2$, $C_3F_7$—O—$CF_2$—$CF$=$CF_2$, $C_4F_9$—O—$CF_2$—$CF$=$CF_2$, $CF_2$=$CF$—O—$(CF_2)_5$—O—$CF$=$CF_2$, $CF_2$=$CF$—$CF_2$—O—$(CF_2)_5$—O—$CF_2$—$CF$=$CF_2$, $CF_2$=$CF$—O—$(CF_2)_4$—CN, X—$(CF_2)_3$—X (with X independently selected from I and Br), or combinations thereof.

Embodiment 36

The method according to any one of embodiments 1 to 35, wherein the fluorinated compound converted into an acyl fluoride compound comprises 1,1,1,2,2,3,3-heptafluoro-3-({1,1,1,2,3,3-hexafluoro-3-[(trifluoroethenypoxy]propan-2-yl}oxy)propane (PPVE-2).

Embodiment 37

A compound selected from:

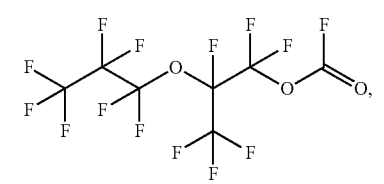

(1)

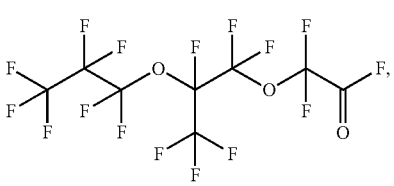

(2)

derivatives thereof, or combinations thereof.

The invention claimed is:

1. A method of converting a fluorinated compound into a fluorinated acyl fluoride, the method comprising:
   reacting the fluorinated compound with a catalytic amount of at least one transition metal compound selected from the group consisting of an oxide, a spinel compound, an oxoperoxo metal compound, and oxoperoxo metal complex with organic complexing agents, and a combination thereof; and an oxygen-containing compound to form the fluorinated acyl fluoride,
   wherein the transition metal compound comprises Ti, V, Cr, Mn, Fe, Co, Ni, Zr, Nb, Mo, Ru, Rh, Pd, Hf, Ta, W, Re, Os, Ir, Pt, or combinations thereof; and
   wherein the wherein the oxygen-containing compound comprises an oxygen-containing gas comprising oxygen ($O_2$), ozone ($O_3$), nitrous oxide ($N_2O$), or combinations thereof.

2. The method according to claim 1, wherein the fluorinated compound comprises at least one epoxide group.

3. The method according to claim 1, wherein the fluorinated compound comprises at least one ether group.

4. The method according to claim 1, wherein the fluorinated compound is a fluorinated olefin containing compound.

5. The method according to claim 1, wherein the fluorinated compound is a partially fluorinated four carbon chain compound, partially fluorinated five carbon chain compound, partially fluorinated six carbon chain compound, perfluorinated four carbon chain compound, perfluorinated five carbon chain compound, perfluorinated six carbon chain compound, or combinations thereof.

6. The method according to claim 1, wherein the fluorinated compound is a perfluorinated vinyl ether compound.

7. The method according to claim 1, wherein the fluorinated compound is a cyclic fluorinated olefin.

8. The method according to claim 1, wherein the transition metal compound comprises vanadium oxide ($V_2O_5$), molybdenum oxide ($MoO_3$), or combinations thereof.

9. The method according to claim 1, wherein the transition metal compound comprises vanadium oxide ($V_2O_5$).

10. The method according to claim 1, wherein the catalytic amount of the transition metal compound is not greater than 20 mol % transition metal oxide based on the total mols of the olefin.

11. The method according to claim 1, wherein the catalytic amount of the transition metal compound is 1 mol % to 5 mol % transition metal oxide based on the total moles of the olefin.

12. The method according to claim 1, wherein the oxygen-containing gas comprises $O_2$.

13. The method according to claim 1, wherein the reaction is carried out at a temperature of not less than 50° C.

14. The method according to claim 13, wherein the reaction is carried out at a temperature from 50° C. to 650° C.

15. The method according to claim 1, wherein the fluorinated acyl fluoride is

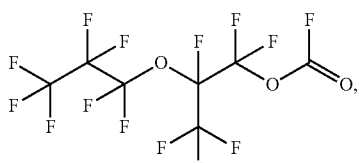

(1)

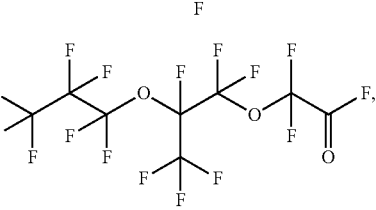

(2)

or combinations thereof.

16. The method according to claim 1 further comprising hydrolyzing the fluorinated acyl fluoride.

17. The method according to claim 16, wherein the hydrolysis occurs at temperatures greater than room temperature.

18. The method according to claim 1 further comprising esterifying the fluorinated acyl fluoride.

19. The method according to claim 18, wherein esterifying occurs by reacting the fluorinated acyl fluoride with an alcohol.

20. The method according to claim 19, wherein the alcohol is selected from methanol, ethanol, propanol, or combinations thereof.

21. The method according to claim 1, wherein the fluorinated compound converted into an acyl fluoride compound comprises 1,1,1,2,2,3,3-heptafluoro-3-({1,1,1,2,3,3-hexafluoro-3-[(trifluoroethenyl)oxy]propan-2-yl}oxy)propane (PPVE-2).

22. The method of claim 1, wherein the transition metal compound comprises V, Nb, Ta, Cr, Mo, W or combinations thereof.

23. The method according to claim 1 further comprising reacting the fluorinated acyl fluoride with an iodine containing compound to form a chain transfer agent.

24. The method according to claim 1 further comprising reacting the fluorinated acyl fluoride with other fluoride containing reagents to form vinyl- or allyl-ethers, bisolefins, or nitrile containing compounds.

25. The method according to claim 1 further comprising reacting the fluorinated acyl fluoride with hexafluoropropene oxide (HFPO), a perfluoro allyl fluorosulfate, or combinations thereof to form vinyl-ethers, allyl-ethers, or combinations thereof.

* * * * *

UNITED STATES PATENT AND TRADEMARK OFFICE
CERTIFICATE OF CORRECTION

PATENT NO. : 10,737,998 B2
APPLICATION NO. : 16/065454
DATED : August 11, 2020
INVENTOR(S) : Hirschberg et al.

It is certified that error appears in the above-identified patent and that said Letters Patent is hereby corrected as shown below:

On the Title Page

Item (72)
Line 10, Fifth Inventor, Delete "Romana Pajkert, Breman (DE);" and insert -- Romana Pajkert, Bremen (DE); --, therefor.
Line 11, Sixth Inventor, Delete "Sergey Tverdomed, Breman (DE)" and insert -- Sergey Tverdomed, Bremen (DE) --, therefor.

Item (57), Abstract
Line 8, Delete "<Insert chemical formulas here as they appear in the electronic copy.> and derivatives thereof, or combinations thereof.".
Below the chemical formulas (1) and (2), insert -- and derivative thereof, or combinations thereof. --.

In the Specification

Column 5
Line 11, Delete "—$CF_2$—$]_x$—" and insert -- —$CF_2$—$O]_x$— --, therefor.
Line 18 (Approx.), Delete "$CF_2$=C—O—" and insert -- $CF_2$=CF—O— --, therefor.

Column 15
Line 21, Delete "-[(trifluoroethenypoxy]propan-2-" and insert
-- -[(trifluoroethenyl)oxy]propan-2- --, therefor.

In the Claims

Column 22
Line 9, In Claim 1, delete "wherein the wherein the" and insert -- wherein the --, therefor.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*